(12) United States Patent
Chen et al.

(10) Patent No.: US 9,826,979 B2
(45) Date of Patent: Nov. 28, 2017

(54) INTRODUCER AND CIRCULAR STAPLER

(71) Applicant: Suzhou Touchstone International Medical Science Co., Ltd., Suzhou (CN)

(72) Inventors: Wangdong Chen, Suzhou (CN); Min Sun, Suzhou (CN); Shuicheng Ding, Suzhou (CN); Zongshun Wang, Suzhou (CN); Wei Xu, Suzhou (CN); Kai Liu, Suzhou (CN)

(73) Assignee: Suzhou Touchstone International Medical Science Co., Ltd., Suzhou (CN)

( * ) Notice: Subject to any disclaimer, the term of this patent is extended or adjusted under 35 U.S.C. 154(b) by 834 days.

(21) Appl. No.: 14/187,773

(22) Filed: Feb. 24, 2014

(65) Prior Publication Data

US 2014/0191012 A1 Jul. 10, 2014

Related U.S. Application Data

(63) Continuation-in-part of application No. PCT/CN2012/080507, filed on Aug. 23, 2012.

(30) Foreign Application Priority Data

Aug. 24, 2011 (CN) .......................... 2011 1 0243515
Aug. 16, 2012 (CN) .......................... 2012 1 0291684
Aug. 16, 2012 (CN) .......................... 2012 1 0291706

(51) Int. Cl.
*A61B 17/115* (2006.01)
*A61B 17/34* (2006.01)
*A61B 90/00* (2016.01)

(52) U.S. Cl.
CPC ........ *A61B 17/1155* (2013.01); *A61B 17/115* (2013.01); *A61B 2017/3452* (2013.01);
(Continued)

(58) Field of Classification Search
USPC .......................................... 227/176.1, 175.1
See application file for complete search history.

(56) References Cited

U.S. PATENT DOCUMENTS 7,182,239 B1 * 2/2007 Myers .................. A61B 17/115
227/175.1
2006/0229566 A1 10/2006 Hanagasaki
(Continued)

FOREIGN PATENT DOCUMENTS

CN 201676016 U 12/2010
CN 101991449 A 3/2011
(Continued)

OTHER PUBLICATIONS

Extended European Search Report dated Jul. 17, 2015 for EP Application No. 12825317.6.

*Primary Examiner* — Michelle Lopez
*Assistant Examiner* — Chinyere Rushing-Tucker
(74) *Attorney, Agent, or Firm* — Fox Rothschild LLP

(57) ABSTRACT

An introducer for being fitted with a circular stapler, is a flexible plastic member in a whole shape of conical with an inner cavity; the introducer has a proximal end and a distal end, outer diameter of the introducer is gradually increased from the distal end to the proximal end and a maximum outer diameter of the proximal end is less than or equal to a maximum outer diameter of a staple cartridge assembly; when pulled by an external force, the plastic member may be unwound spirally and finally forms a strip body capable of being disengaged from the circular stapler. The introducer provided by the present disclosure has the advantages that: as the maximum outer diameter of the introducer is approximately equal to the maximum outer diameter of the staple cartridge assembly, the process of introducing can be achieved without bad influence resulting from increasing the outer diameter of the circular stapler. Moreover, the intro- (Continued)

ducer can be pulled out from the circular stapler in one piece in the form of a strip, so that the operation is convenient and no additional step can be added for the subsequent operation of the circular stapler.

30 Claims, 15 Drawing Sheets

(52) U.S. Cl.
 CPC . *A61B 2090/037* (2016.02); *A61B 2090/0807* (2016.02); *A61B 2090/08021* (2016.02)

(56) References Cited

U.S. PATENT DOCUMENTS

| | | | |
|---|---|---|---|
| 2007/0075117 A1 | 4/2007 | Milliman et al. | |
| 2008/0172087 A1 | 7/2008 | Fuchs et al. | |
| 2009/0204108 A1* | 8/2009 | Steffen | A61B 17/068 606/1 |
| 2010/0163598 A1 | 7/2010 | Belzer | |
| 2011/0036888 A1 | 2/2011 | Pribanic et al. | |
| 2011/0114697 A1* | 5/2011 | Baxter, III | A61B 17/115 227/175.1 |
| 2011/0114698 A1 | 5/2011 | Baxter, III et al. | |
| 2014/0203064 A1* | 7/2014 | Chen | A61B 17/1155 227/176.1 |

FOREIGN PATENT DOCUMENTS

| | | |
|---|---|---|
| CN | 102048569 A | 5/2011 |
| CN | 201855287 U | 6/2011 |
| CN | 202218890 U | 5/2012 |
| CN | 202313535 U | 7/2012 |
| CN | 202821483 U | 3/2013 |
| DE | 2928635 A1 | 2/1981 |
| JP | 2007503888 A | 3/2007 |
| JP | 2007523691 A | 8/2007 |
| WO | 2004032766 A2 | 4/2004 |
| WO | 2008089404 A2 | 7/2008 |

* cited by examiner

INTRODUCER AND CIRCULAR STAPLER

The present is a continuation-in-part of International application Ser. No. PCT//CN12/80507, filed Aug. 23, 2012, which claims priority to Chinese patent application No. 201110243515.0, entitled "introducer", filed with the State Intellectual Property Office of P.R.China on Aug. 24, 2011; Chinese patent application No. 201210291684,6, entitled "double spiral introducer", filed with the State intellectual Property Office of P.R.China on Aug. 16, 2012; and Chinese patent application No. 201210291706.9, entitled "introducer", filed with the State Intellectual Property Office of P,R.China on Aug. 16, 2012. The contents of the foregoing applications are hereby incorporated by reference in their entireties.

TECHNICAL FIELD

The present disclosure relates to a surgical auxiliary member for a circular stapler, in particular to an introducer for the circular stapler.

BACKGROUND

The circular stapler is a surgical instrument widely used in stitching and cutting operations on tubular tissue. The circular stapler comprises a circular stapling head assembly and an actuating assembly. After placing two sections of tubular tissue to be joined together between an anvil and a staple cartridge of the stapling head assembly, a distance between the anvil and the staple cartridge is then adjusted to tightly clamp two sections, and next, the actuating member is operated to fire the staples and join the two sections of tissue together.

In actual operation procedures, when performing two operations, i.e. lower rectal operation and gastric bypass operation, the circular stapler is difficult to enter tubular tissue. In the lower rectal operation, a circular stapler with the diameter of 33 mm, which must be performed via anus, is adopted. As the anus is a muscular opening and has small diameter in normal state, large-diameter instrument is very difficult to be inserted into the anus. In the gastric bypass operation, a circular stapler with the diameter of 25 mm, which must be performed in small intestine, is adopted. As the small intestine is an alimentary canal of the human body, there are a lot of mucous membranes in the inner wall thereof. However, the circular stapler has large end surface and the surface is not smooth enough due to the structural features. Therefore, the mucous membranes tend to be damaged when the circular stapler is moved through the small intestine.

To solve the above problems, a plurality of auxiliary instruments sleeved around the periphery of a staple cartridge assembly of a circular stapler was developed in the prior art, which are disclosed in U.S. patent publication Nos. US2009/0204108 and US2011/0114698. By means of the auxiliary instrument, the staple cartridge assembly of the circular stapler can be introduced into the human body and moved through intestinal tracts; and the auxiliary instrument can be disengaged from the staple cartridge assembly after the circular stapler arrives at a predetermined surgical position, without any influence on the subsequent procedures of the circular stapler. The current auxiliary instruments can help surgeons to smoothly place a head of the stapler into the predetermined position, but they must be torn and pulled out by large force. Thereby, tissues tend to be damaged accidentally, and hence, the use experience is poor. Moreover, as the auxiliary instruments are all sleeved around the periphery of the staple cartridge assembly, the outer diameter of the instrument is certain to be larger than that of the stapler, and thereby having an opposite effect of aggravating the pain of patients.

SUMMARY

The objective of the present disclosure is to solve the above technical problem and provide an introducer with simple structure and easy manipulation, without additionally increasing the outer diameter of a stapler, and thereby alleviating the sufferings of patients.

In one aspect of the present disclosure, there is provided an introducer for being fitted with a circular stapler, the circular stapler comprising an anvil assembly, a staple cartridge assembly, a circular pipe fixed at a proximal end of the staple cartridge assembly, and a trocar movably disposed in the staple cartridge assembly and for connection with the anvil assembly, the staple cartridge assembly including a staple cylinder and a staple cartridge being mutually fixed, and a cutter and a staple pusher movably disposed in the staple cylinder, a distal end of the staple cartridge being formed with a staple cartridge surface opposite to the anvil assembly, the staple cylinder being provided with at least one guide hole, wherein the introducer is a flexible plastic member in a whole shape of conical with a hollow cavity; the introducer has a proximal end and a distal end, outer diameter of the introducer is gradually increased from the distal end to the proximal end and a maximum outer diameter of the proximal end is less than or equal to a maximum outer diameter of the staple cartridge assembly; when pulled by an external force, the plastic member is unwound spirally and finally forms a strip body capable of being disengaged from the circular stapler via the guide hole.

Preferably, when pulled by an external force, the plastic member may be unwound spirally in a sequence from distal to proximal.

Preferably, a central tube may be protruded inwards from bottom of a distal end of the hollow cavity of the introducer; and inner diameter of the central tube may be equal to outer diameter of a distal end of the trocar.

Preferably, a traction hole for connecting with a traction member may be formed on a wall at a proximal end of the central tube which is also one end of the whole flexible plastic member.

Preferably, a plane for being attached to the staple cartridge surface may be formed at the proximal end of the introducer.

Preferably, a cylinder is protruded outwards on the plane, outer diameter of the cylinder may be equal to inner diameter of the cutter, and outer peripheral surface of the cylinder is attached to an inner side face of the cutter.

Preferably, a proximal end of the cylinder may be the other end of the whole flexible plastic member, and a chromatic area for indication may be coated at the other end of the flexible plastic member.

Preferably, the traction hole may be formed on a convex bar which is protruded on the central tube toward the proximal end of the introducer.

Preferably, connecting ribs may be perpendicularly arranged between adjacent spiral wires of the spiral flexible plastic member.

Preferably, a plane for being attached to the staple cartridge surface may be formed at the proximal end of the introducer, and positioning columns connected and fixed to the staple cartridge surface may be perpendicularly extended on the plane.

Preferably, circular holes with a diameter approximately equal to that of the positioning columns or staple holes for accommodating staples therein may be formed on the staple cartridge surface, for matching with the positioning columns.

Preferably, the positioning column may include a fastening arm which has a length greater than or equal to the depth of the staple hole, and a latching teeth which is disposed at a proximal end of the positioning column and has a width in a diameter direction of the introducer greater than a width of the corresponding staple hole in the diameter direction of the introducer.

Preferably, at least one pair of the positioning columns may be disposed symmetrically in the diameter direction of the introducer.

Preferably, two latching tooth of each pair of the positioning columns may be extended in opposite directions.

Preferably, the latching teeth may comprise a stopper portion and a bend portion which is connected between the stopper portion and the fastening arm and has a width W2 less than or equal to the width W3 of the fastening arm in the diameter of the introducer.

Preferably, the positioning column may be made of deformable material.

Preferably, a projection having an outer diameter increasing from its proximal end to its distal end may be provided at top of the distal end of the introducer.

Preferably, the projection may be provided with a perforation, an inner diameter of a distal end hole of which is larger than an inner diameter of a proximal end hole thereof.

Preferably, a conical wall of the introducer may include a first flexible strip and a second flexible strip which are attached with each other and arranged alternately and spirally, so that when pulled by an external force, the conical wall is unwound spirally in the sequence from distal to proximal and finally forms a strip body which can be disengaged from the circular stapler and consists of the first flexible strip and the second flexible strip via the guide hole.

Preferably, the first flexible strip may be made of rigid material, the second flexible strip may be made of soft material, and the first flexible strip and the second flexible strip may be mutually attached by bonding or over-molding.

Preferably, a clamping portion may be extended outwards from a proximal end of the conical wall, and outer diameter of the clamping portion may be less than or equal to inner diameter of the staple cylinder.

Preferably, a traction member may be disposed at a distal end of the first flexible strip; the traction member may be a traction string fixed at the distal end of the first flexible strip, or the traction member with a free end extended toward a proximal end of the circular stapler may be an extension of the distal end of the first flexible strip.

Preferably, a conical wall of the introducer may include an inner layer and an outer layer, wherein the first layer is a spiral body formed by the winding of first flexible strip, the second layer is a second membrane layer covering on the first layer, so that when pulled by an external force, the second membrane layer together with the first flexible strip are unwound spirally in the sequence from distal to proximal and finally forms a strip body capable of being disengaged from the circular stapler via the guide hole.

Preferably, the first flexible strip may be tightly and spirally arranged, and the second membrane layer may be only covering on the outside or the inside of the conical wall.

Preferably, the first flexible strip may be spirally arranged, the second membrane layer may be covering on the outside or the inside of the conical wall, and partial second membrane layer may be extended into between spiral wires of the wound first flexible strip, so that the first flexible strip and the second membrane layer are alternately and spirally arranged and tightly attached with each other.

Preferably, the first flexible strip may be made of rigid material, the second membrane layer may be made of soft material, and the first flexible strip and the second membrane layer may be mutually attached by bonding or over-molding.

Preferably, a clamping portion with outer diameter less than or equal to inner diameter of the staple cylinder may be extended outwards from a proximal end of the conical wall.

Preferably, a traction member may be disposed at a distal end of the first flexible strip; the traction member may be a traction string fixed at the distal end of the first flexible strip, or the traction member with a free end extended toward a proximal end of the circular stapler may be an extension of the distal end of the first flexible strip.

Preferably, connecting ribs may be perpendicularly arranged between adjacent spiral wires of the first flexible strip.

There is further provided an introducer for being fitted with a circular stapler, the circular stapler comprising an anvil assembly, a staple cartridge assembly and a circular pipe fixed at a proximal end of the staple cartridge assembly, the staple cartridge assembly including a staple cylinder and a staple cartridge being mutually fixed, and a cutter and a staple pusher movably disposed in the staple cylinder, a distal end of the staple cartridge being formed with a staple cartridge surface opposite to the anvil assembly, the staple cylinder being provided with at least one guide hole, wherein the introducer consists of a spiral memory metal wire formed by integral winding and silica gel coated on the periphery of the spiral memory metal wire, the introducer has a proximal end and a distal end, outer diameter of the introducer is gradually increased from the distal end to the proximal end, and a maximum outer diameter of the proximal end is less than or equal to outer diameter of the staple cartridge or the staple cylinder; when pulled by an external force, the spiral memory metal wire is unwound spirally in a sequence from distal to proximal and finally forms a strip body capable of being disengaged from the circular stapler via the guide hole.

Preferably, outline of the introducer from the distal end to the proximal end may be conical with a hollow inner cavity; a traction member with one end connected with the spiral memory metal wire may be extended out from inside bottom of the distal end of the introducer.

Preferably, the traction member may be one part of the spiral memory metal wire, and one end of the traction member used for pulling and holding may be one end of the whole spiral memory metal wire.

Preferably, a plane for being attached to the staple cartridge surface may be formed at the proximal end of the introducer.

Preferably, a cylinder may be protruded outwards on the plane, outer diameter of the cylinder may be equal to inner diameter of the cutter, and an outer peripheral surface of the cylinder may be attached to an inner side face of the cutter.

Preferably, a proximal end of the cylinder may be the other end of the whole spiral memory metal wire.

Preferably, connecting ribs may be perpendicularly arranged between adjacent spiral wires of the silica gel on the periphery of the spiral memory metal wire.

The introducer provided by the present disclosure has the advantages that:

The maximum outer diameter of the introducer is equal to or less than the maximum outer diameter of the staple cartridge assembly, so that the introducing can be achieved without bad influence resulting from increasing the outer diameter of the circular stapler and the introducer can be pulled out from the guide hole of the circular stapler in one piece in the form of a strip body, so that the operation is convenient and no additional step can be added for the subsequent operation of the circular stapler.

BRIEF DESCRIPTION OF THE DRAWINGS

Further description will be given below to the technical proposals of the present disclosure with reference to the accompanying drawings.

DETAILED DESCRIPTION OF EMBODIMENTS

Certain exemplary embodiments will now be described to provide an overall understanding of the structure, function, manufacture, and use of the devices and operation process disclosed herein. One or more examples of these embodiments are illustrated in the accompanying drawings. Those of ordinary skill in the art will understand that the features illustrated or described in connection with one exemplary embodiment may be combined with the features of other embodiments. Such modifications and variations are intended to be included within the scope of the present invention.

The terms "proximal" and "distal" are used herein with reference to a clinician manipulating the circular stapler. The term "proximal" refers to be closest to the clinician and the term "distal" refers to be located away from the clinician. The term "conical" is defined a tapered shape, like but not exactly a cone, further including but not limited to conical, truncated conical, hemispherical, etc.

Figure 1:
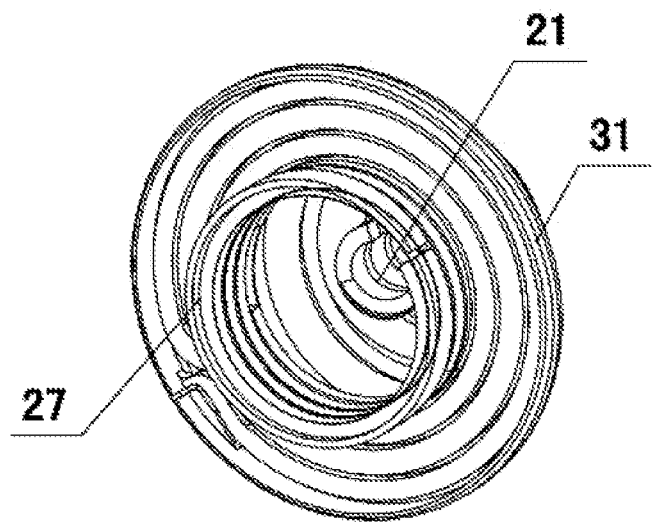
FIG. 1 is a schematic structural view of a first embodiment of the present disclosure.
Figure 2:
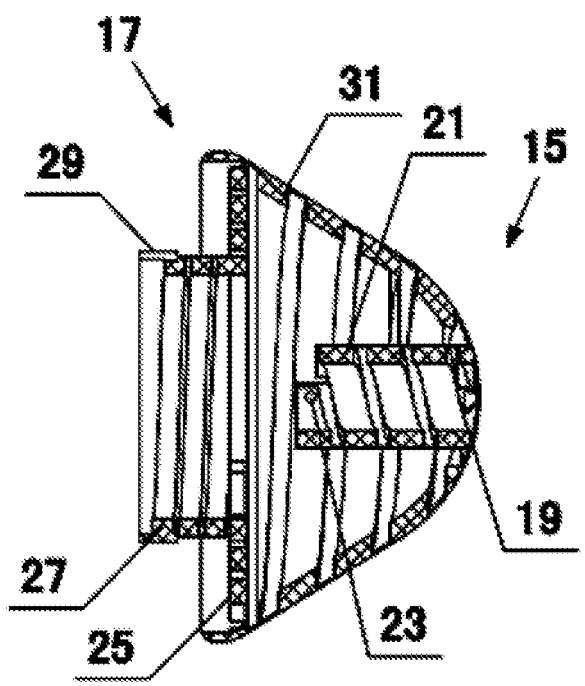
FIG. 2 is a sectional view of the first embodiment of the present disclosure.
Figure 3:
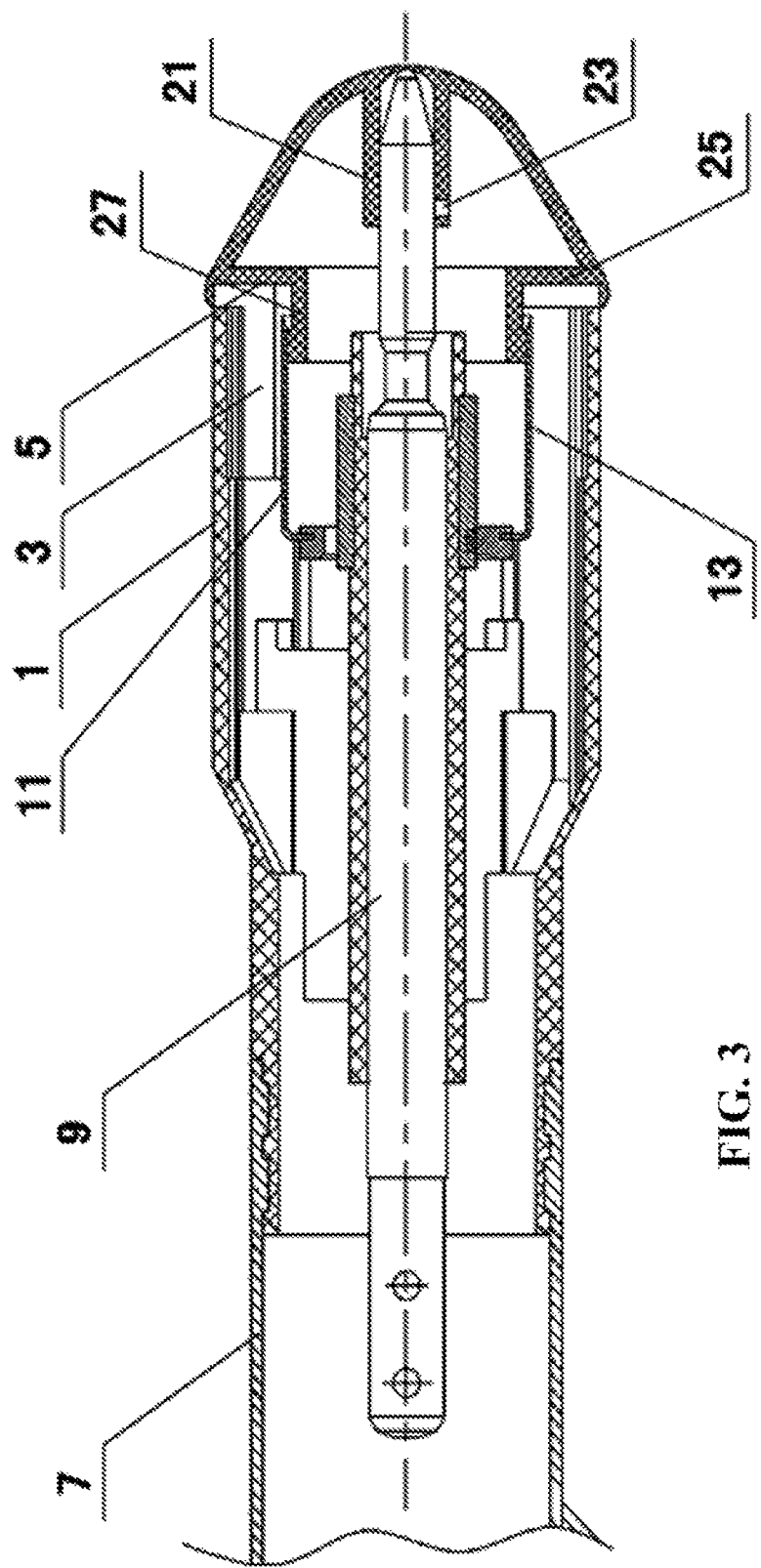
FIG. 3 is a schematic diagram illustrating the state of the first embodiment of the present disclosure fitted with a circular stapler.

The present application discloses an auxiliary instrument for a circular stapler, in particular to an introducer for introducing the circular stapler into the human body, for example, a first embodiment as illustrated in FIGS. 1 to 3.

A circular stapler in the related art comprises an anvil assembly, a staple cartridge assembly, a circular pipe 7 fixed to a proximal end of the staple cartridge assembly, and a trocar 9 movably disposed in the staple cartridge assembly and for connection with the anvil assembly. The staple cartridge assembly includes a staple cylinder 1 and a staple cartridge 3 which are mutually fixed, and a cutter 11 and a staple pusher which are movably disposed in the staple cylinder 1. A staple cartridge surface 5, opposite to an anvil surface of the anvil assembly, is formed at a distal end of the staple cartridge 3. The staple cylinder 1 is provided with at least one guide hole.

In the present disclosure, the introducer is a spiral flexible plastic member formed by integral winding. That is, the introducer is a spiral member, like a spring, formed by the integral winding of a flexible plastic material. The introducer is just a section of "spring wire".

As shown in the related drawings, the introducer comprises a proximal end 17 and a distal end 15. Outer diameter of the introducer is gradually increased from the distal end 15 to the proximal end 17, and the outer diameter of the proximal end 17 is equal to the outer diameter of the staple cartridge 3 or the staple cylinder 1. That is, the proximal end 17, a middle section 31 and the distal end 15 of the introducer form a conical spring, and the maximum outer diameter of the bottom of the conical spring is equal to the outer diameter of the staple cartridge 3 or the staple cylinder 1. Certainly, the maximum outer diameter of the bottom of the conical spring may be less than the outer diameter of the staple cartridge 3 or the staple cylinder 1; alternatively, the maximum outer diameter of the bottom of the conical spring may be slightly greater than the outer diameter of the staple cartridge 3 or the staple cylinder 1.

As illustrated in FIG. 2, the outline of the introducer from the distal end 15 to the proximal end 17 is conical with a hollow inner cavity. As a flexible plastic member wound to be the introducer may be made of rubber or other plastics, the "spring wire" of the introducer may be made to have different thicknesses depending on different level process, resulting in the inner cavities of the introducer with different dimensions.

In the embodiment, a central tube 21 is protruded inwards at the bottom 19 of a distal end 15 of the hollow inner cavity of the introducer; and the inner diameter of the central tube 21 is equal to the outer diameter of a distal end of the trocar 9. Therefore, in the initial state, the introducer may be sleeved around the trocar 9 by the central tube 21, so that the introducer can be fitted with the circular stapler. Thus, when the introducer together with the circular stapler is introduced into the human body, the trocar can well support the introducer, thereby preventing the top of the distal end of the introducer from collapsing.

A traction hole 23 is formed on a wall at a proximal end of the central tube 21; and the proximal end of the central tube 21 is one end of the whole flexible plastic member, namely one end of the "spring wire".

A plane 25, to be attached to the staple cartridge surface 5, is formed at the proximal end of the introducer. A cylinder 27, with an outer diameter equal to the inner diameter of the cutter 11, is protruded outwards from the plane 25. An outer peripheral surface 29 of the cylinder 27 is attached to an inner side face 13 of the cutter. Moreover, a proximal end of the cylinder 27 is the other end of the whole flexible plastic member, namely the other end of the "spring wire". A chromatic area, generally in yellow, having different color with the whole introducer, is coated at the end, generally by spraying method, for indicating the end portion.

In the operation process with the first embodiment, firstly, the introducer is engaged with a distal end of the staple cartridge assembly; then, the circular stapler is introduced into the human body; and next, a traction string connected to a traction hole is pulled so that the introducer is unwound spirally in a sequence of from distal to proximal and hence pulled out from the circular stapler in one piece in the form of a strip via the guide hole on the staple cylinder, which is similar to the state of pulling the "spring wire" into a straight wire. Due to the yellow area, when a surgeon sees the yellow area, it is indicated that the introducer has been completely pulled out from the circular stapler. Additionally, as the maximum outer diameter of the introducer is approximately equal to the maximum outer diameter of the staple cartridge assembly, the process of introducing can be achieved without the bad influence resulting from increasing the outer diameter of the circular stapler.

In a variation of this embodiment, the position of the traction hole may be changed to a proximal end of the cylinder 27. And hence, In condition that the trocar 9 is supporting the introducer, the introducer may be unwound spirally in a sequence from proximal to distal and hence pulled out from the circular stapler in one piece in the form of a strip via the guide hole of the staple cartridge.

Figure 4:
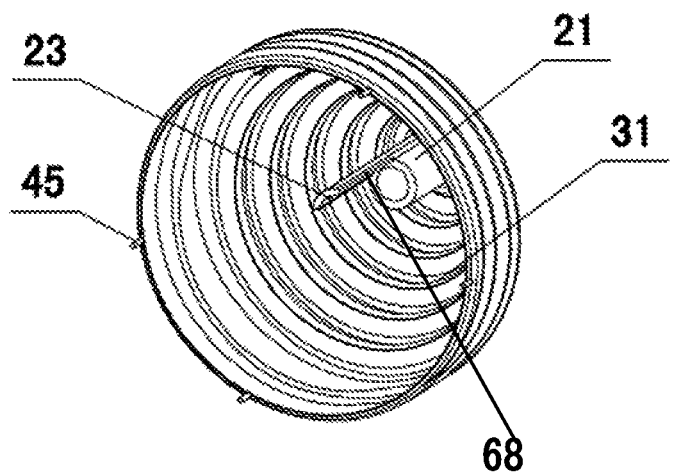
FIG. 4 is a schematic structural view of a second embodiment of the present disclosure.
Figure 5:
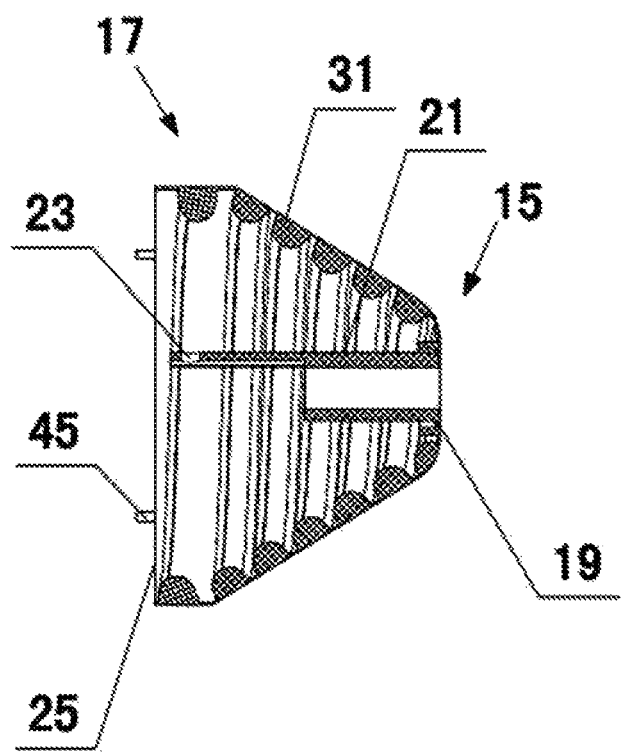
FIG. 5 is a sectional view of the second embodiment of the present disclosure.

FIGS. 4 and 5 illustrate the second embodiment of the present disclosure. The difference of the second embodiment from the first embodiment is that: the traction hole 23 is formed on a convex bar 68, protruded on the central tube toward the proximal end of the introducer.

In the present embodiment, no cylinder is at the proximal end of the introducer, which not only saves the materials but also facilitate the manufacture of the introducer. Similarly, the introducer in the initial position can be fixed on the trocar 9 via the central tube 21. In order to better match the introducer to the circular stapler, in the present embodiment, positioning columns 45 for being connected and fixed to the staple cartridge surface 5 are perpendicularly extended on the plane 25, and small circular holes with a diameter approximately equal to that of the positioning column 45 are formed on the staple cartridge surface. As the operation method of the embodiment is the same as that of the first embodiment, no further description will be given herein.

Figure 6:
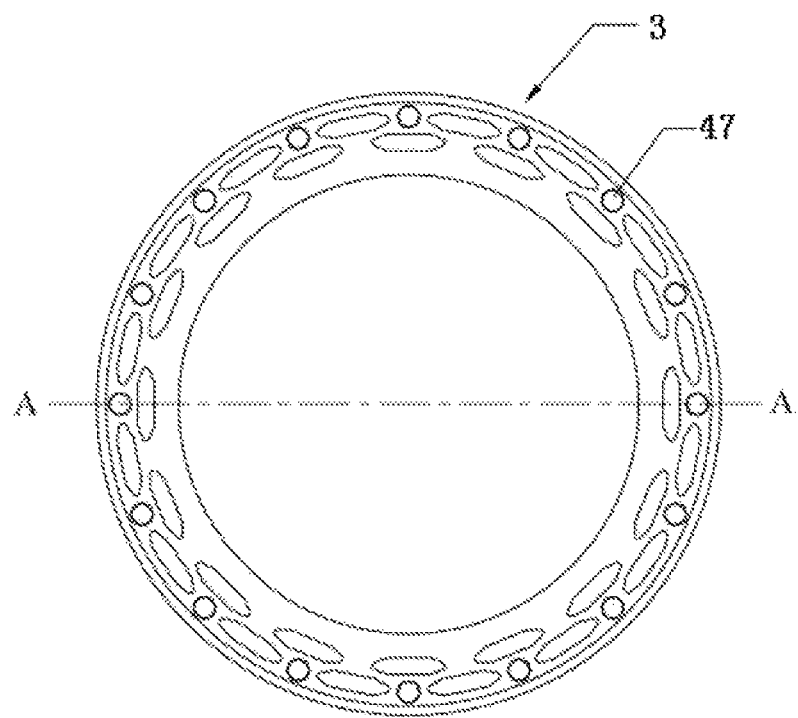
FIG. 6 is a top view of the staple cartridge of the second embodiment of the present disclosure.
Figure 7:
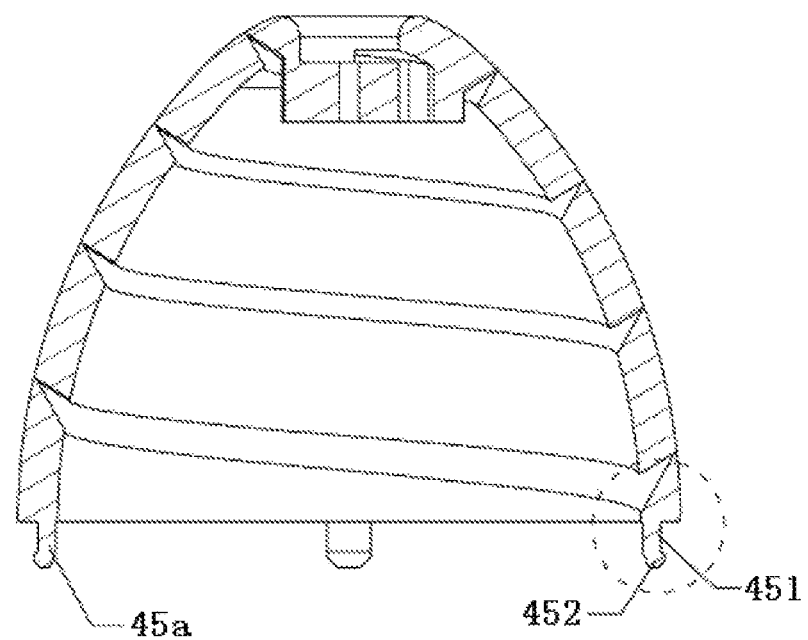
FIG. 7 is a sectional view of a variation of the second embodiment of the present disclosure.

As for the hole on the staple cartridge surface, as shown in FIG. 6, it may be a blind hole 47 matched with the positioning column 45, for example, with an interference fit. The positioning column has air-releasing grooves thereon by which the air in the blind hole 47 is compelled out. Due to the pressure difference between the outside and inside of the hole, and due to the great friction between the positioning column 45 and inner wall of the blind hole 47, the introducer is well fitted with the staple cartridge of the circular stapler.

FIGS. 7~13 illustrate a variation of the second embodiment of the present disclosure. A positioning column 45a is provided on the proximal end of the introducer. The positioning column 45a can be fitted with a staple hole 47a on the staple cartridge of the circular stapler. By the match between the positioning column 45a and a staple hole 47a, the introducer can be well-mounted on the circular stapler, without separation from the circular stapler during the process of introducing. It should be noted that the term "staple hole" herein refers to a hole for receiving the staple on the staple cartridge surface, which has existed in the traditional circular staple, without any require to change the structure of the staple cartridge.

Figure 8:
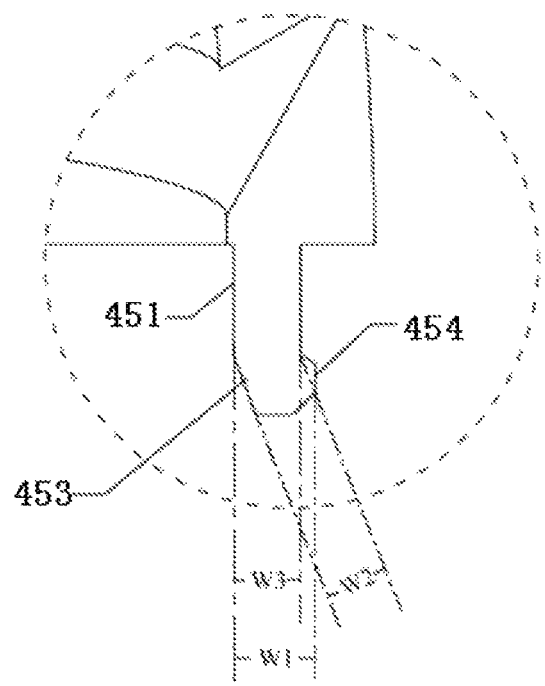
FIG. 8 is an enlarged view illustrating the structure of a part in dashed line of FIG. 7 in the present disclosure.
Figure 9:
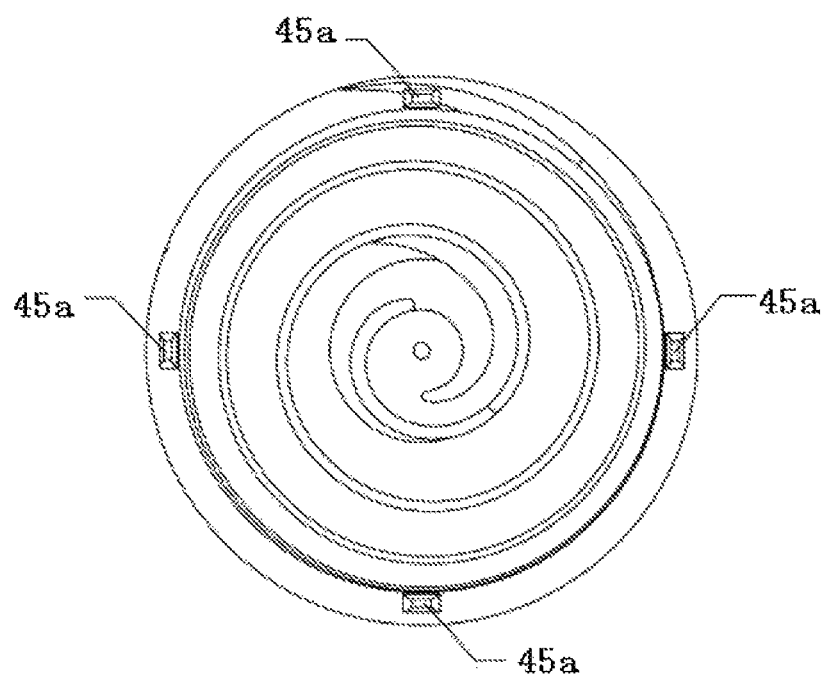
FIG. 9 is a bottom view of the variant embodiment of FIG. 7 in the present disclosure.
Figure 10:
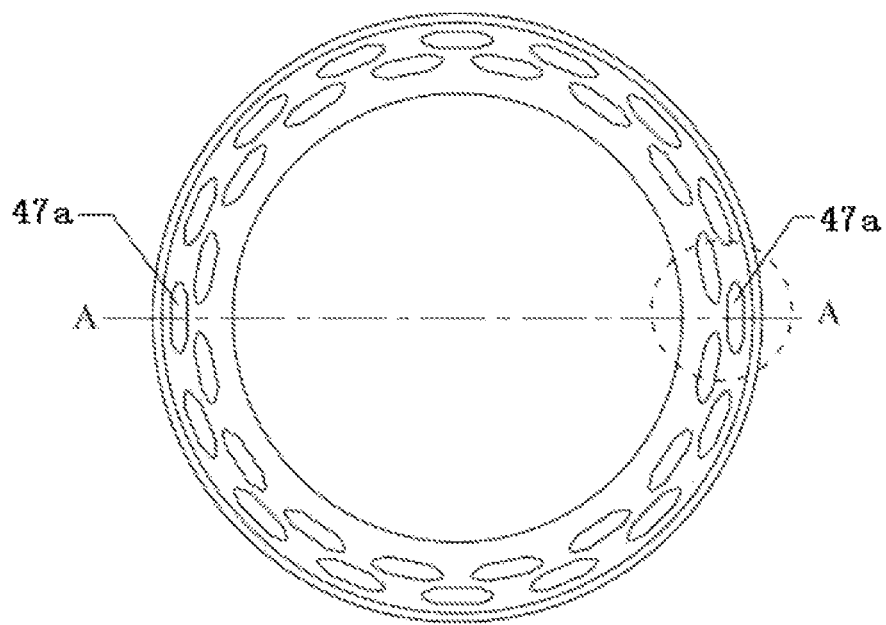
FIG. 10 is a top view of the staple cartridge of the variant embodiment of FIG. 7 in the present disclosure.
Figure 11:
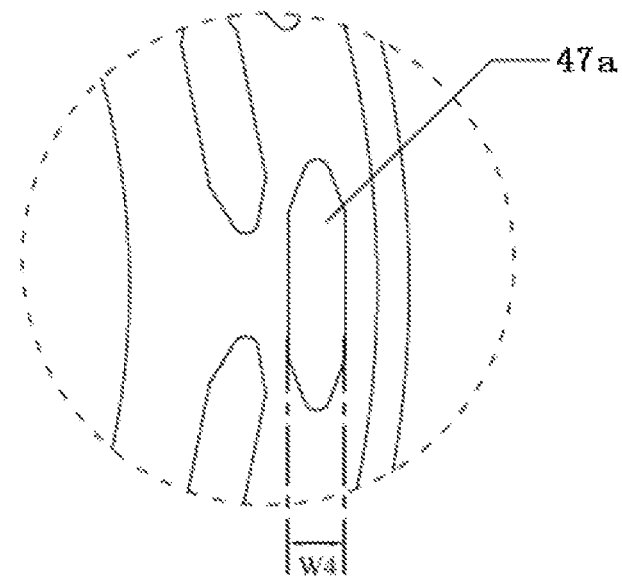
FIG. 11 is an enlarged view illustrating the structure of a part in dashed line of FIG. 10 in the present disclosure.

As can be seen in FIG. 8, FIG. 9 and FIG. 11, the introducer is also a spiral structure as a whole, formed by winding a spiral wire. The positioning column 45a of the introducer includes a fastening arm 451 which has a length greater than or equal to the depth of the staple hole 47a, and a latching teeth 452 which is disposed at a proximal end of the positioning column 45a and has a width W1 in a diameter direction of the introducer greater than a width W4 of the corresponding staple hole 47a in the diameter direction of the introducer. In a preferred embodiment, the length of the fastening arm 451 is equal to the depth of the staple hole 47a, so as to limit the movement of the introducer along an axial direction of the circular stapler.

The introducer has at least one pair of positioning columns 45a which may be disposed symmetrically in the diameter direction of the introducer, and two latching tooth 452 of each pair of the positioning columns 45a are extended in opposite directions. In a preferred embodiment, the introducer has two pairs of positioning columns 45a which are disposed symmetrically at the diameter direction of the introducer and arranged evenly in a circumferential direction of the introducer, thereby with better fastening effect.

The positioning column 45a is made of deformable material. The latching teeth 452 comprises a stopper portion 454 and a bend portion 453 which is connected between the stopper portion 454 and the fastening arm 451 and has a width W2 less than or equal to the width W3 of the fastening arm 451 along the diameter of the introducer. Due to configuration of the latching teeth 452, a certain of resistance force may exist at the beginning of assembling the introducer onto the circular stapler, i.e. when the positioning column 45a is just inserted into the corresponding staple hole 47a of the staple cartridge; but then, the latching teeth 452 tends to deform to be parallel with the fastening arm 451 by the design of the bend portion 453, which is equivalent to the decrease of the width of the latching teeth 452 in the diameter direction of the introducer. Hence, the match operation of the positioning column 45a with the staple hole 47a of the staple cartridge is favorable.

In the above embodiment, the arrangement and configuration of the positioning column and the corresponding hole assure a reliable and detachable fixing of the introducer on the circular staple, with easy manipulation and lower cost, and even without any alteration to the traditional circular staple.

Figure 14:
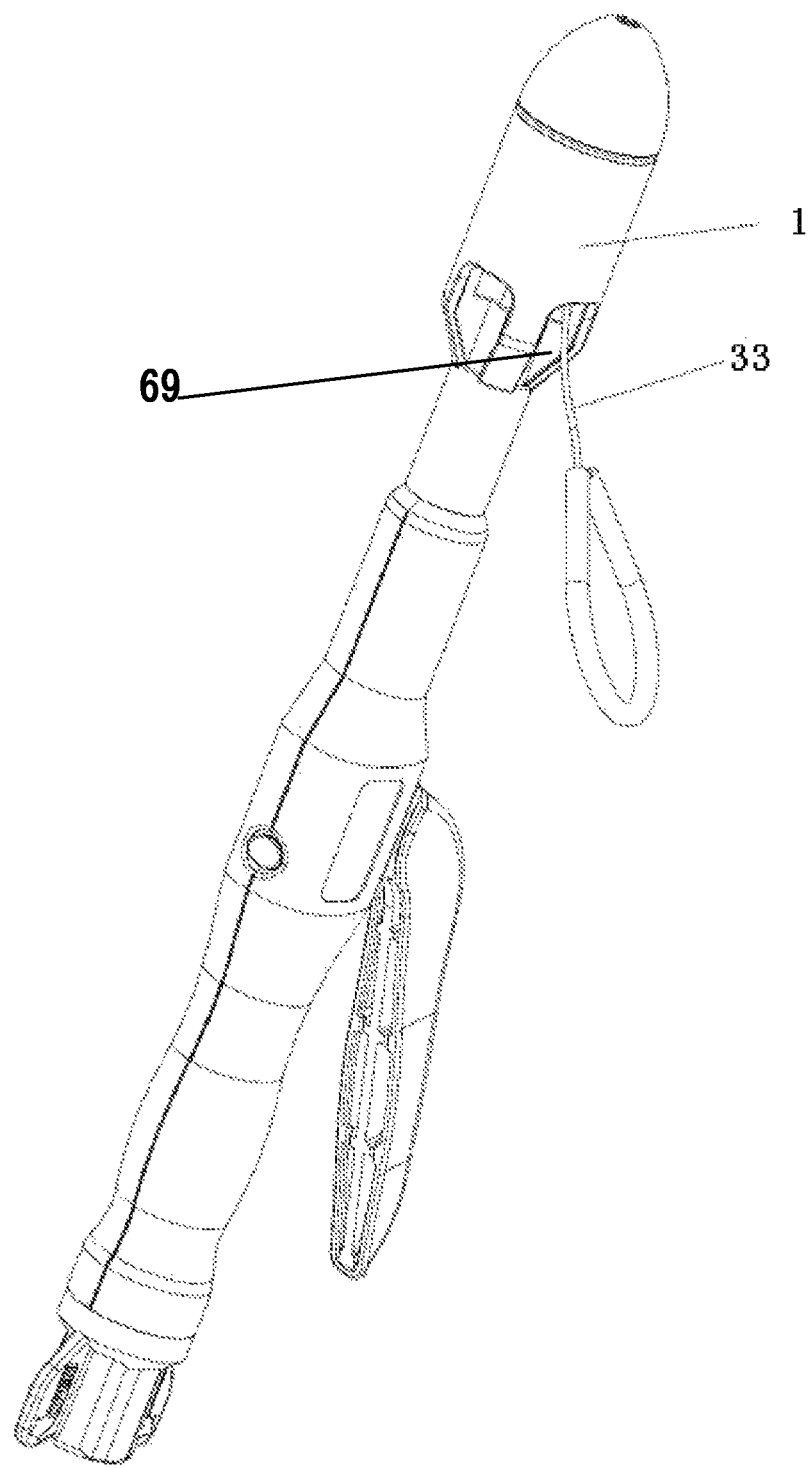
FIG. 14 is a schematic structural view of another variation of second embodiment of the present disclosure attached to a circular stapler.

Referring to FIG. 14, in a variation of the second embodiment, the circular staple comprises a staple body, a staple cylinder assembly disposed on the staple body, and a handle portion pivotally connected with the staple body. An introducer is detachably fitted with the staple cylinder assembly thereon. The staple cylinder assembly includes a staple cylinder provided with at least one guide hole 69 and a staple cartridge fixed on the staple cylinder.

Figure 15:
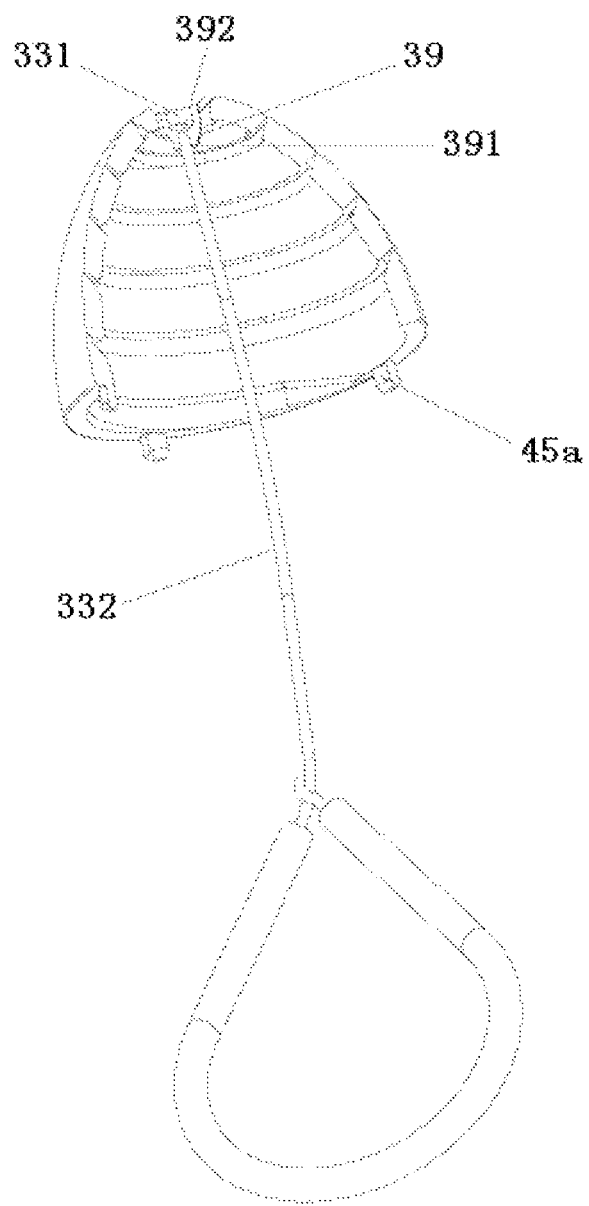
FIG. 15 is a sectional view of the another variation of second embodiment of the present disclosure.

Referring to FIG. 15, a projection 39 is also provided at the top of the distal end of the introducer and it has a proximal end closer to the stapler and a distal end opposite to the proximal end. The projection 39 is in a shape of hollow circular truncated cone with a gradually increasing outer diameter from the proximal end to the distal end thereof. The projection 39 is provided with a perforation, an inner diameter of a distal end hole 392 of which is larger than an inner diameter of a proximal end hole 391 thereof.

The traction member 33 comprises a traction portion 332 and a connecting portion 331 disposed at an end of traction portion 332. The connecting portion 331 can be received in the hollow projection 39. The outer diameter of the connecting portion 331 is less than or equal to the inner diameter of the distal end hole 392 of the projection 39, and is greater than the inner diameter of the proximal end hole 391 of the projection 39. The outer diameter of the traction portion 332 of the traction member 33 is less than or equal to the inner diameter of the proximal end hole 391 of the projection 39.

While mounting the connecting portion 331 of the traction member 33 with the projection 39, the traction member 33 is allowed to be smoothly inserted into the introducer via the distal end hole 392 of the projection 39 since the outer diameter of the traction portion 332 of the traction member 33 is less than or equal to the inner diameter of the proximal end hole 391 of the projection 39. Further, when the connecting portion 331 of the traction member 33 is received in the proximal end 391 of the projection 39, the connecting portion 331 is not allowed to go through the proximal end hole 391 of the projection 39 and hence is blocked in the hollow projection 39, since the outer diameter of the connecting portion 331 is greater than the inner diameter of the proximal end hole 391 of the projection 39, such that one end of the traction member 33 is fitted with the projection 39.

The configuration of the outline of the projection 39 in a shape of hollow circular truncated cone with smooth wall from the proximal end to the distal end thereof results in less interference with a passage in the circular stapler and thereby facilitates a smooth pulling of the spiral wire out from the circular stapler. Additionally, since the projection 39 in a shape of hollow circular truncated cone is disposed at the distal end of the introducer, when pulling the traction member 33, the connecting portion 331 of the traction member 33 blocked in the projection 39 would further pull the projection 39 at an end of the spiral wire to move toward the circular stapler so that the introducer is unwound spirally. Advantageously, the out diameter of the distal end of the projection 39 is less than the passage in the circular stapler through which the traction member 33 goes, such that the spiral wire together with the projection 39 is allowed to be smoothly pulled out of the circular stapler in one piece in the form of a strip. Furthermore, the projection 39 is configured to be hollow to provide an accommodation for receiving the traction member 33.

Figure 16:
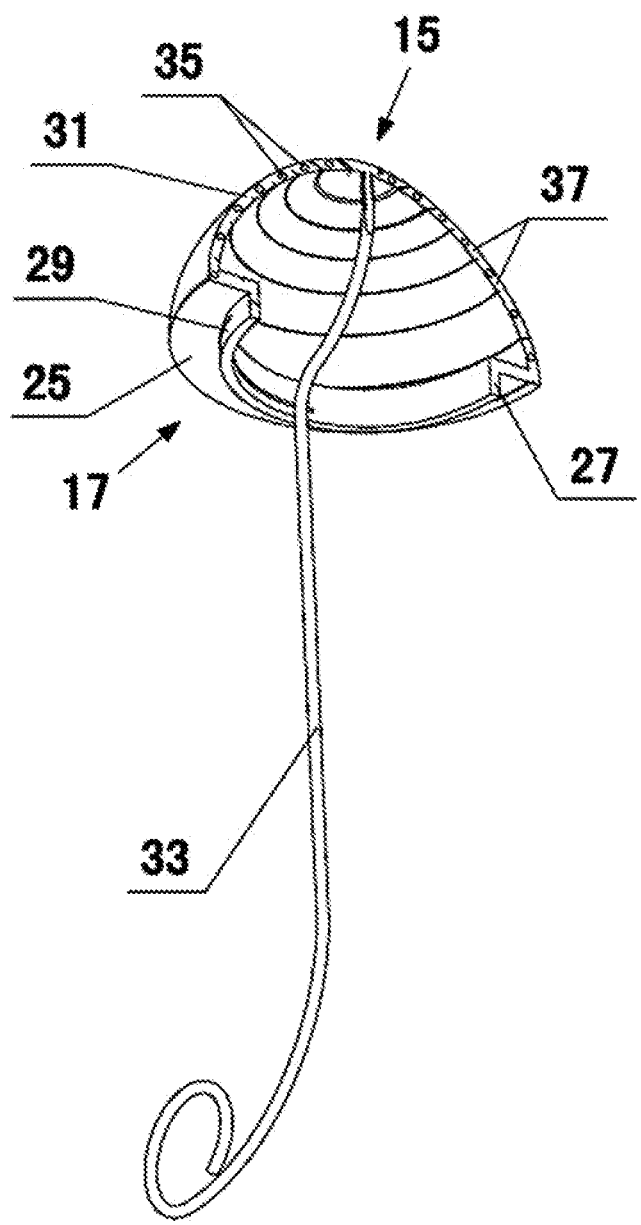
FIG. 16 is a schematic structural view of a third embodiment of the present disclosure.

FIG. 16 illustrates the third embodiment of the present disclosure. In the embodiment, the introducer consists of spiral memory metal wire 35 formed by integral winding and silica gel 37 coated on the periphery of the spiral memory metal wire 35. The introducer comprises a proximal end 17 and a distal end 15. Outer diameter of the introducer is gradually increased from the distal end 15 to the proximal end 17, and the outer diameter of the proximal end 17 is equal to the outer diameter of the staple cartridge 3 or the staple cylinder 1.

The memory metal wire 35 is configured to be spiral conical shape in the embodiment, which may have the introducing function, but the introducing effect is poor as the memory metal wires 35 are relatively soft. Therefore, one layer of silica gel 37 is coated on the periphery of the memory metal wire 35. Moreover, the silica gels 37 on the periphery of adjacent "spring wires" are mutually bonded, so that the acting force to a plurality of introducers in the human organism can be dispersed.

In the embodiment, the outline of the introducer from the distal end 15 to the proximal end 17 is configured to be a conical spring with a hollow inner cavity. A traction member 33, with one end connected with the spiral memory metal wire 35, is extended out from the bottom of the inside of the distal end 15 of the introducer. Certainly, the most direct mode may be that: the traction member 33 may be one part of the spiral memory metal wire 35, and one end of the traction member 33 for pulling and holding by hand may be just one end of the whole spiral memory metal wire 35. Therefore, not only the traction hole in the first embodiment may be omitted, but also the spiral shape of the memory metal wires 35 can be simply manufactured in one piece.

A plane 25 to be attached to the staple cartridge surface is formed at the proximal end 17 of the introducer. A cylinder 27 with an outer diameter equal to the inner diameter of the cutter 11 is protruded outwards from the plane 25. An outer peripheral surface of the cylinder 27 is attached to an inner side face 13 of the cutter. A proximal end of the cylinder 27 is the other end of the whole flexible plastic member.

In the operation process with the third embodiment, firstly, the introducer is engaged with a distal end of the staple cartridge assembly; then, the circular stapler is introduced into the human body; and next, the traction member is pulled so that the memory metal wires can be pulled out from the guide hole of the circular stapler in one piece in the form of a strip. Meanwhile, as the maximum outer diameter of the introducer is approximately equal to the maximum outer diameter of the staple cartridge assembly, the process of introducing can be achieved without bad influence resulting from increasing the outer diameter of the circular stapler. Moreover, as the memory metal wire haves restore function, the introducer of the embodiment can be reused after disinfected.

Figure 17:
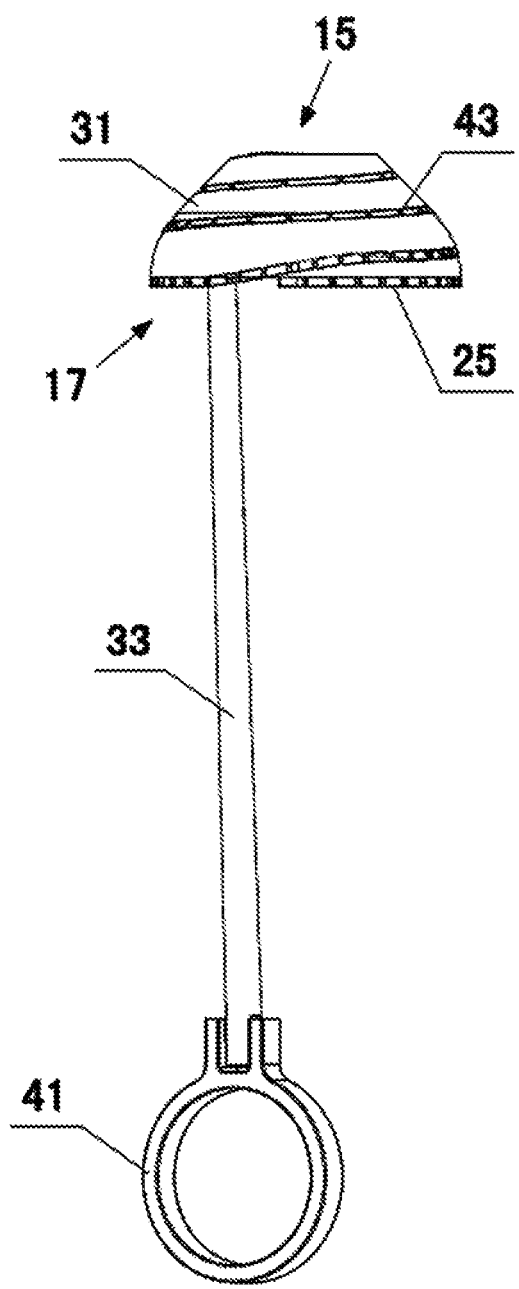
FIG. 17 is a schematic structural view of a fourth embodiment of the present disclosure.
Figure 18:
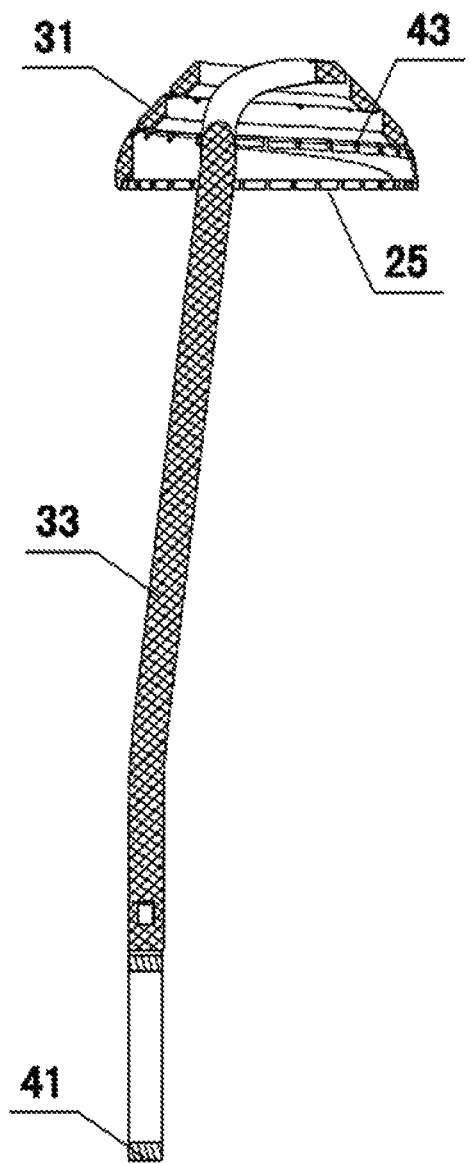
FIG. 18 is a sectional view of the fourth embodiment of the present disclosure.

FIGS. 17 and 18 illustrate the fourth embodiment of the present disclosure. The main difference of the embodiment is that: connecting ribs 43 are perpendicularly disposed between adjacent "spiral wires" of the introducer. When pulling, the connecting ribs can be easily pulled apart, which is similar to current common plastic bottle caps. Due to the arrangement of the connecting ribs 43, the strength of the introducer in the shape of the "spiral wire" can be larger. Certainly, the connecting ribs 43 may be disposed on the spiral flexible plastic member of the first embodiment and the second embodiment, and may also be disposed on the silica gel on the periphery of the spiral memory metal wires. Certainly, the connecting ribs 43 may also be disposed on the "spiral wires" in other shapes.

The structure of the traction member will be described in detail in the embodiment. The traction member 33 is led out from the inside of the distal end of the introducer and extended out from an inner cavity formed by the encircling of the proximal end and the distal end of the introducer. A pull ring 41 is disposed at one end of the traction member 33. The pull ring is placed outside of the circular stapler, and a finger of a surgeon may have the access to the pull ring.

In the above embodiments, the introducer is pulled out from the inside of the stapler, namely at least one guide hole, preferably 4 guide holes, are formed on the staple cylinder of the circular stapler. The introducer is unwound in the form of a strip and disengaged from the circular stapler via the guide holes. Certainly, the above embodiments may also be changed to be pulled out from the outside of the stapler, provided that a connecting position of the traction member on the introducer is changed.

Figure 19:
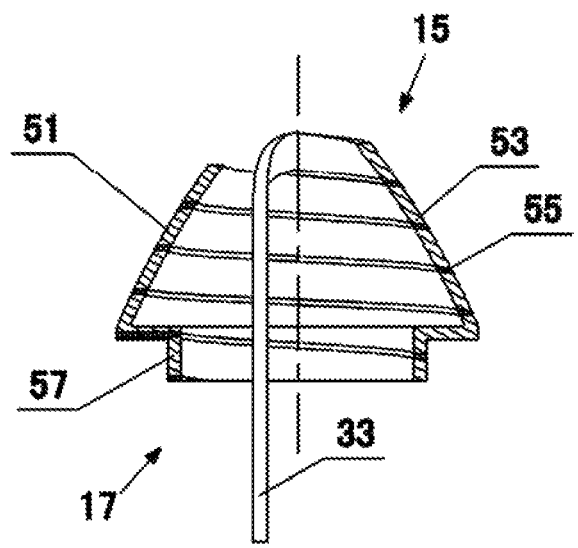
FIG. 19 is a schematic structural view of a fifth embodiment of the present disclosure.
Figure 20:
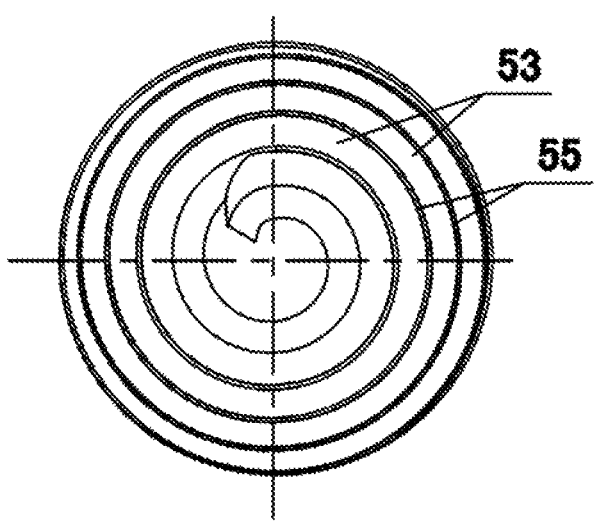
FIG. 20 is a top view of the fifth embodiment of the present disclosure.

FIGS. 19 and 20 illustrate the fifth embodiment of the present disclosure. The characteristics of the embodiment are as follows. A conical wall 51 of the introducer includes a first flexible strip 53 and a second flexible strip 55 which are parallel to each other and wound to form a spiral body; and the first flexible strip 53 and the second flexible strip 55 are attached with each other and alternately and spirally arranged. The first flexible strip 53 is made of relatively rigid material, thereby with higher strength and higher hardness; and the second flexible strip 55 is made of relatively soft material, thereby with lower strength and being easily torn. There are various types of medical plastics, e.g. polyvinylchloride (PVC), polyethylene (PE), polypropylene (PP), polyethylene terephthalate (PET), polyurethane (PU), polystyrene (PS), polycarbonate (PC) and polytetrafluoroethylene (PTFE), and the only condition for selecting the material is to satisfy the above strength. Moreover, the first flexible strip 53 and the second flexible strip 55 are mutually attached by bonding or over-molding.

A clamping portion 57 is extended outwards from a proximal end 17 of the conical wall 51, namely extended towards a proximal end of the circular stapler. The outer diameter of the clamping portion 57 is less than or equal to the inner diameter of the staple cylinder 1. Therefore, the clamping portion 57 is clamped on the inside of the staple cylinder 1, so that the introducer can be fitted at a distal end of the staple cylinder of the circular stapler. As the maximum diameter of the conical wall 51 is almost equal to the maximum diameter of the staple cylinder, the outer diameter is not increased after the introducer is fitted with the staple cylinder 1 of the circular stapler, and hence it is more convenient to insert the circular stapler into the body.

In the embodiment, as the first flexible strip 53 and the second flexible strip 55 are mutually and tightly wound, the conical wall 51 of the whole introducer has higher strength and hence would not be collapsed when the circular stapler is introduced into the body of a patient. Moreover, as the first flexible strip 53 and the second flexible strip 55 are mutually and tightly wound, the outside of the conical wall 51 of the whole introducer is relatively smooth, so that the outer wall would not scratch the tissue when the circular stapler is introduced into the body of a patient, with much better effect than that of single spiral flexible strip.

A traction member 33 is also disposed at a distal end of the first flexible strip 53. The traction member 33 is an extension of the distal end of the first flexible strip 53, and a free end of the traction member 33 is extended toward the proximal end of the circular stapler. Alternatively, the traction member 33 may also be a traction string fixed at the distal end of the first flexible strip 53 as long as the pulling function can be achieved. At least one guide hole is formed on the staple cylinder of the circular stapler, and the traction member 33 in the initial state runs through the guide hole.

In the operation process, firstly, the introducer of the preferred embodiment is engaged with a distal end of the staple cartridge assembly; then, the circular stapler is introduced into the human body, and at this moment, the free end of the traction member 33 runs through the guide hole and is exposed out of the body of a patient; and next, the traction member 33 is pulled so that the first flexible strip 53 is unwound spirally in a sequence from distal to proximal and finally form a strip body consisted of the first flexible strip and the second flexible strip, and pulled out from the circular stapler in one piece via the guide hole, which is similar to the state of pulling the "spring wire" into a straight wire. In this process, as the second flexible strip 55 has lower strength, it can be easily pulled apart, and broken bodies of the second flexible strip 55 together with the first flexible strip 53 can be pulled out from the circular stapler. Certainly, the above embodiment may also be changed to be pulled out from the outside of the stapler as long as the connecting position of the traction member on the introducer is changed.

Figure 21:
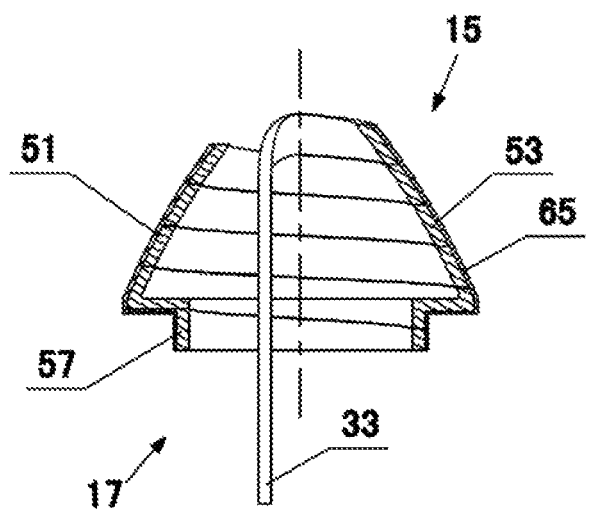
FIG. 21 is a schematic structural view of a sixth embodiment of the present disclosure.
Figure 22:
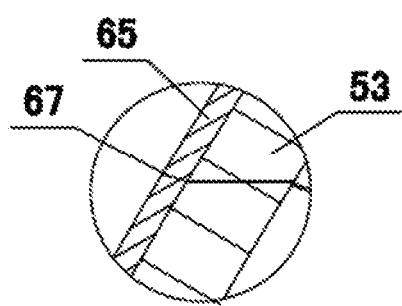
FIG. 22 is a partial enlarged view illustrating the state when the sixth embodiment of the present disclosure is torn.
Figure 23:
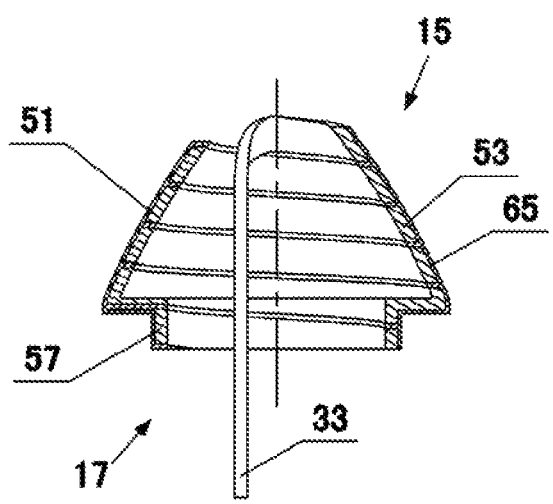
FIG. 23 is a schematic structural view of a seventh embodiment of the present disclosure.

FIGS. 21 and 22 illustrate the sixth embodiment of the present disclosure. The characteristics of the embodiment are that: the conical wall 51 of the introducer includes an inner layer and an outer layer; the inner first layer is a spiral body formed by the winding of first flexible strip 53; and the outer second layer is a second membrane layer 65 covering on the outside of the first layer. Certainly, the case that the spiral body formed by the winding of the first flexible strip 53 is disposed outside and the second membrane layer 65 covering on the inside of the first layer is disposed inside is not excluded from the scope of the present disclosure. In the embodiment, the first flexible strip 53 is tightly and spirally arranged, and the second membrane layer 65 is only covering on the outside of the conical wall 51. In the seventh embodiment as illustrated in FIG. 23, the first flexible strip 53 is spirally arranged, the second membrane layer 65 is covering on the outside of the conical wall 51, and partial second membrane layer 65 is extended into between spiral wires of the first flexible strip 53, so that the first flexible strip 53 and the second membrane layer 65 are attached with each other and arranged alternately and spirally.

The first flexible strip 53 is made of relatively rigid materials, thereby with higher strength and higher hardness; and the second membrane layer 65 is made of relatively soft material, thereby with lower strength and being easily torn. Moreover, the first flexible strip 53 and the second membrane layer 65 are mutually attached by bonding or over-molding.

In the sixth embodiment and the seventh embodiment, a clamping portion 57 is also extended outwards from the proximal end 17 of the conical wall 51, namely extended toward the proximal end of the circular stapler. The outer diameter of the clamping portion 57 is less than or equal to the inner diameter of the staple cylinder 1. Therefore, the clamping portion 57 is clamped on the inside of the staple cylinder 1, so that the introducer can be fitted at a distal end of the staple cylinder of the circular stapler. As the maximum diameter of the conical wall 51 is almost equal to the maximum diameter of the staple cylinder, the outer diameter is not increased after the introducer is fitted with the stapler cylinder 1 of the circular stapler, and hence it is more convenient to insert the circular stapler into the body. A traction member 33 is also disposed at a distal end of the first flexible strip 53. The traction member 33 is an extension of the distal end of the first flexible strip 53, and a free end of the traction member 33 is extended toward the proximal end of the circular stapler. Alternatively, the traction member 33 may also be a traction string fixed at the distal end of the first flexible strip 53 as long as the pulling function can be achieved. At least one guide hole is formed on the staple cylinder of the circular stapler, and the traction member 33 in the initial state runs through the guide hole.

As the first flexible strip 53 are tightly wound in the sixth embodiment and the first flexible strip 53 and partial membrane layer 65 are tightly wound in the seventh embodiment, the conical wall 51 of the whole introducer has relative high strength and hence would not be collapsed when the circular stapler is introduced into the body of a patient. Moreover, as the second membrane layer 65 is completely covering on the outside of the first flexible strip 53, the outside of the conical wall 51 of the whole introducer is relatively smooth, so that the outer wall would not scratch the tissue when the circular stapler is introduced into the body of a patient, thereby with much better effect than that of single spiral flexible strip.

The operation method of the sixth embodiment is identical with that of the seventh embodiment. Description will be given below by taking the sixth embodiment as an example.

Figure 12:
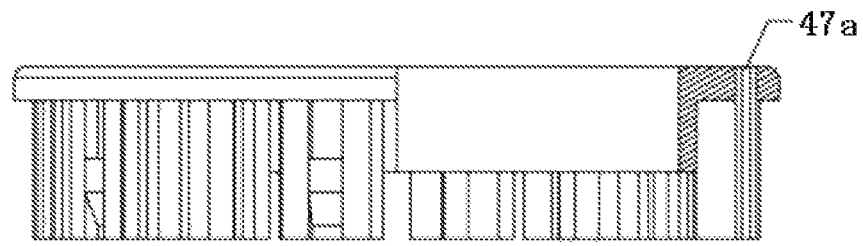
FIG. 12 is a partial sectional view along A-A direction in FIG. 10 of the present disclosure.
Figure 13:
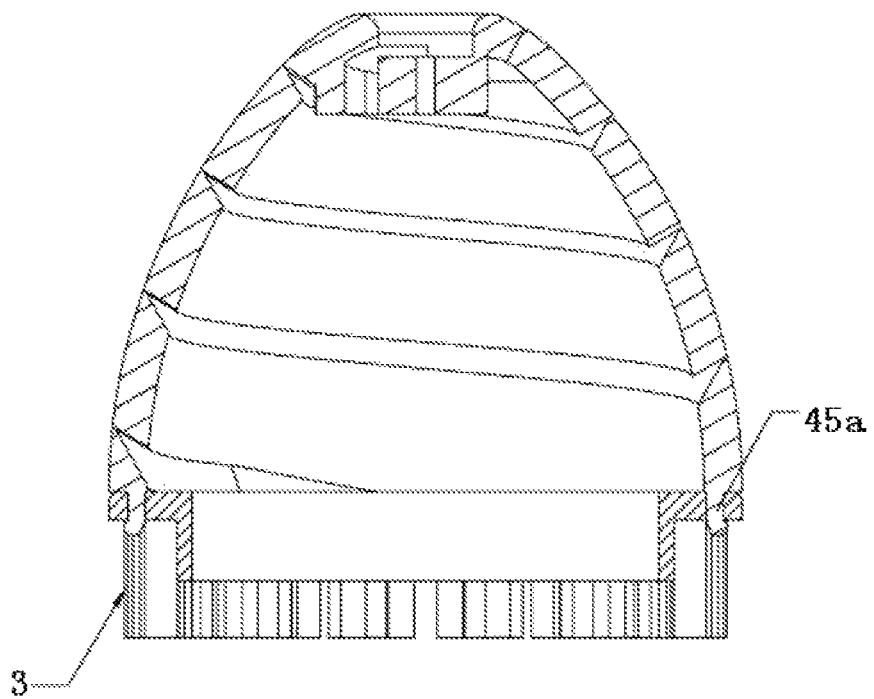
FIG. 13 is a sectional view of the staple cartridge combined with the variant embodiment of FIG. 7 in the present disclosure.

In the operation process, firstly, the introducer of the preferred embodiment is engaged with at a distal end of the staple cartridge assembly; then, the circular stapler is introduced into the body, and at this moment, a free end of the traction member 33 runs through the guide hole and is exposed out of the body of a patient; and next, the traction member 33 is pulled so that the second membrane layer 65 together with the first flexible strip 53 are unwound spirally in the sequence from distal to proximal and finally forms a strip body which is pulled out from the circular stapler in one piece via the guide hole, which is similar to the state of pulling the "spring wire" into a straight wire. In the process, as the second membrane layer 65 has relative low strength and hence is easily pulled apart, so that a tear line 67 of the second membrane layer 65 as illustrated in FIG. 12 occurs near two adjacent spiral wires of the wound first flexible strip 53, and a broken body of the second membrane layer 65 can be pulled out from the circular stapler together with the first flexible strip 53. Certainly, the above embodiment may also be changed to be pulled out from the outside of the stapler as long as the connecting position of the traction member on the introducer is changed.

As similar to the first embodiment, in the above embodiments, a chromatic area, particularly in yellow, for being distinguished with the whole introducer, is formed at the proximal end of the introducer, generally by spraying method. The chromatic area is used for indicating the doctor that the whole introducer has been completely removed out of the circular stapler. Due to the yellow area, when the surgeon sees the yellow area, it is indicated that the introducer has been completely pulled out from the circular stapler.

The introducer in the present disclosure has simple operation and the introducer can be disengaged from the circular stapler in one step. However, in the related art, the process requires multi-step operation, and the spring wires of the introducer cannot be released in the form of a strip and hence can easily scratch the tissue.

The introducer in the present disclosure may also have various embodiments. All the technical proposals formed by equivalent replacements or variations to the disclosed embodiments should fall within the scope of protection of the present disclosure.

What is claimed is:

1. An introducer for being fitted with a circular stapler, the circular stapler comprising an anvil assembly, a staple cartridge assembly, a circular pipe fixed at a proximal end of the staple cartridge assembly, and a trocar movably disposed in the staple cartridge assembly and for connection with the anvil assembly, the staple cartridge assembly including a staple cylinder and a staple cartridge being mutually fixed, and a cutter and a staple pusher movably disposed in the staple cylinder, a distal end of the staple cartridge being formed with a staple cartridge surface opposite to the anvil assembly, the staple cylinder being provided with at least one guide hole, wherein:

the introducer is a flexible plastic member, the whole shape of the introducer is a conical shape with a hollow cavity; the introducer has a proximal end and a distal end, outer diameter of the introducer is gradually increased from the distal end to the proximal end and a maximum outer diameter of the proximal end is less than or equal to a maximum outer diameter of the staple cartridge assembly; the plastic member is connected with a traction member, the traction member extends in the cavity of the plastic member to connect with the plastic member, when the traction member is pulled by an external force, the plastic member is pulled towards the guide hole of the circular stapler by the traction member and through the cavity which causes the plastic member to be unwound internally and spirally and finally to form a strip body to be withdrawn from the circular stapler via the guide hole.

2. The introducer according to claim 1, wherein the traction member extends in the cavity of the plastic member to connect with the distal end of the plastic member, when the traction member is pulled by an external force, the plastic member is unwound spirally in a sequence from distal to proximal.

3. The introducer according to claim 1, wherein a central tube is protruded inwards from bottom of a distal end of the hollow cavity of the introducer; and inner diameter of the central tube is equal to outer diameter of a distal end of the trocar.

4. The introducer according to claim 3, wherein a traction hole for connecting with the traction member is formed on a wall at a proximal end of the central tube which is also one end of the whole flexible plastic member.

5. The introducer according to claim 4, wherein a plane for being attached to the staple cartridge surface is formed at the proximal end of the introducer.

6. The introducer according to claim 5, wherein a cylinder is protruded outwards on the plane, outer diameter of the cylinder is equal to inner diameter of the cutter, and outer peripheral surface of the cylinder is attached to an inner side face of the cutter.

7. The introducer according to claim 6, wherein a proximal end of the cylinder is the other end of the whole flexible plastic member, and a chromatic area for indication is coated at the other end of the flexible plastic member.

8. The introducer according to claim 4, wherein the traction hole is formed on a convex bar which is protruded on the central tube toward the proximal end of the introducer.

9. The introducer according to claim 1, wherein connecting ribs are perpendicularly arranged between adjacent spiral wires of the spiral flexible plastic member.

10. The introducer according to claim 1, wherein a plane for being attached to the staple cartridge surface is formed at the proximal end of the introducer, and positioning columns connected and fixed to the staple cartridge surface are perpendicularly extended on the plane.

11. The introducer according to claim 10, wherein circular holes with a diameter approximately equal to that of the positioning columns or staple holes for accommodating staples therein are formed on the staple cartridge surface, for matching with the positioning columns.

12. The introducer according to claim 11, wherein the positioning column includes a fastening arm which has a length greater than or equal to a depth of the corresponding hole, and a latching tooth which is disposed at a proximal end of the positioning column and has a width in a diameter direction of the introducer greater than a width of the corresponding hole in the diameter direction of the introducer.

13. The introducer according to claim 12, wherein at least one pair of the positioning columns are disposed symmetrically in the diameter direction of the introducer.

14. The introducer according to claim 13, wherein two latching teeth of each pair of the positioning columns are extended in opposite directions.

15. The introducer according to claim 13, wherein the latching tooth comprises a stopper portion and a bend portion which is connected between the stopper portion and the fastening arm and has a width W2 less than or equal to the width W3 of the fastening arm in the diameter of the introducer.

16. The introducer according to claim 12, wherein the positioning column is made of deformable material.

17. The introducer according to claim 1, wherein a projection having an outer diameter increasing from its proximal end to its distal end is provided at top of the distal end of the introducer.

18. The introducer according to claim 17, wherein the projection is provided with a perforation, an inner diameter of a distal end hole of which is larger than an inner diameter of a proximal end hole thereof.

19. The introducer according to claim 1, wherein a conical wall of the introducer includes a first flexible strip and a second flexible strip which are attached with each other and arranged alternately and spirally, so that when pulled by an external force, the conical wall is unwound spirally in a sequence from distal to proximal and finally forms a strip body which can be disengaged from the circular stapler and consists of the first flexible strip and the second flexible strip via the guide hole.

20. The introducer according to claim 19, wherein the first flexible strip is made of rigid material, the second flexible strip is made of soft material, and the first flexible strip and the second flexible strip are mutually attached by bonding or over-molding.

21. The introducer according to claim 19, wherein a clamping portion is extended outwards from a proximal end of the conical wall, and outer diameter of the clamping portion is less than or equal to inner diameter of the staple cylinder.

22. The introducer according to claim 19, wherein a traction member is disposed at a distal end of the first flexible strip; the traction member is a traction string fixed at the distal end of the first flexible strip, or the traction member with a free end extended toward a proximal end of the circular stapler is an extension of the distal end of the first flexible strip.

23. The introducer according to claim 1, wherein a conical wall of the introducer includes an inner layer and an outer layer, wherein the first layer is a spiral body formed by the winding of first flexible strip, the second layer is a second membrane layer covering on the first layer, so that when pulled by an external force, the second membrane layer together with the first flexible strip are unwound spirally in a sequence from distal to proximal and finally forms a strip body capable of being disengaged from the circular stapler via the guide hole.

24. The introducer according to claim 23, wherein the first flexible strip is tightly and spirally arranged, and the second membrane layer is only covering on the outside or the inside of the conical wall.

25. The introducer according to claim 23, wherein the first flexible strip is spirally arranged, the second membrane layer is covering on the outside or the inside of the conical wall, and partial second membrane layer is extended into between spiral wires of the wound first flexible strip, so that the first flexible strip and the second membrane layer are alternately and spirally arranged and tightly attached with each other.

26. The introducer according to claim 23, wherein the first flexible strip is made of rigid material, the second membrane layer is made of soft material, and the first flexible strip and the second membrane layer are mutually attached by bonding or over-molding.

27. The introducer according to claim 23, wherein a clamping portion with outer diameter less than or equal to inner diameter of the staple cylinder is extended outwards from a proximal end of the conical wall.

28. The introducer according to claim 23, wherein a traction member is disposed at a distal end of the first flexible strip; the traction member is a traction string fixed at the distal end of the first flexible strip, or the traction member with a free end extended toward a proximal end of the circular stapler is an extension of the distal end of the first flexible strip.

29. The introducer according to claim 23, wherein connecting ribs are perpendicularly arranged between adjacent spiral wires of the first flexible strip.

30. A circular stapler, which is fitted with an introducer as claimed in claim 1.

* * * * *